(12) United States Patent
Frezza

(10) Patent No.: US 6,416,498 B1
(45) Date of Patent: Jul. 9, 2002

(54) DEVICE FOR AMBULATORY INJECTION WITH CONTROLLED FLOW RATE OF A MEDICINE IN LIQUID FORM

(75) Inventor: Pierre Frezza, Charly (FR)

(73) Assignee: Laboratoire Aguettant (FR)

( * ) Notice: Subject to any disclaimer, the term of this patent is extended or adjusted under 35 U.S.C. 154(b) by 0 days.

(21) Appl. No.: 09/462,288

(22) PCT Filed: Apr. 26, 1999

(86) PCT No.: PCT/FR99/00986

§ 371 (c)(1),
(2), (4) Date: Jan. 5, 2000

(87) PCT Pub. No.: WO99/56804

PCT Pub. Date: Nov. 11, 1999

(30) Foreign Application Priority Data

May 5, 1998 (FR) .............................. 98 05908

(51) Int. Cl.⁷ ............................................... A61M 5/00
(52) U.S. Cl. ..................... 604/207; 604/186; 604/218; 604/246
(58) Field of Search ............................... 604/181, 187, 604/207, 218, 220, 226, 245–246, 131, 151, 152, 154, 186, 208, 890.1, 891.1, 892.1; 222/409

(56) References Cited

U.S. PATENT DOCUMENTS

| 3,964,481 | A | * | 6/1976 | Gourlandt et al. ...... 128/218 A |
|---|---|---|---|---|
| 4,108,177 | A | * | 8/1978 | Pistor ........................ 128/218 |
| 4,329,985 | A | * | 5/1982 | Bonchek ................. 128/214 R |
| 4,583,978 | A | * | 4/1986 | Porat et al. ................. 604/208 |
| 5,147,329 | A | * | 9/1992 | Brannon ..................... 604/231 |
| 5,314,415 | A | * | 5/1994 | Liebert et al. .............. 604/218 |
| 5,522,804 | A | * | 6/1996 | Lynn ........................... 604/191 |
| 5,714,677 | A | * | 2/1998 | Parsy et al. ................... 422/78 |
| 5,722,955 | A | | 3/1998 | Racz |

FOREIGN PATENT DOCUMENTS

DE              350 330 C        3/1922

* cited by examiner

Primary Examiner—Brian L. Casler
Assistant Examiner—Catherine Serke
(74) Attorney, Agent, or Firm—Cantor Colburn LLP

(57) ABSTRACT

This device comprises: a syringe body equipped with an access which may be connected in succession to a filling member, such as a needle, and to an infusion line fitted with a non-return valve to allow liquid to pass from the syringe into the line; a housing mounted so that it can slide in leaktight fashion inside the body so as to vary the volume of a chamber which it delimits with the body of the syringe; an element which, forming a piston, mounted on the housing and in contact with the chamber, is able, according to its position, to create a raised pressure or reduced pressure in the chamber; means for moving the piston-forming element back and forth.

16 Claims, 3 Drawing Sheets

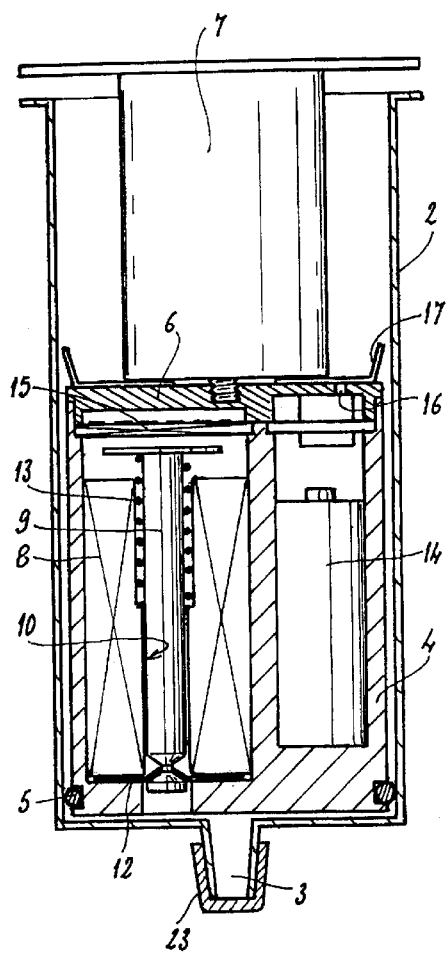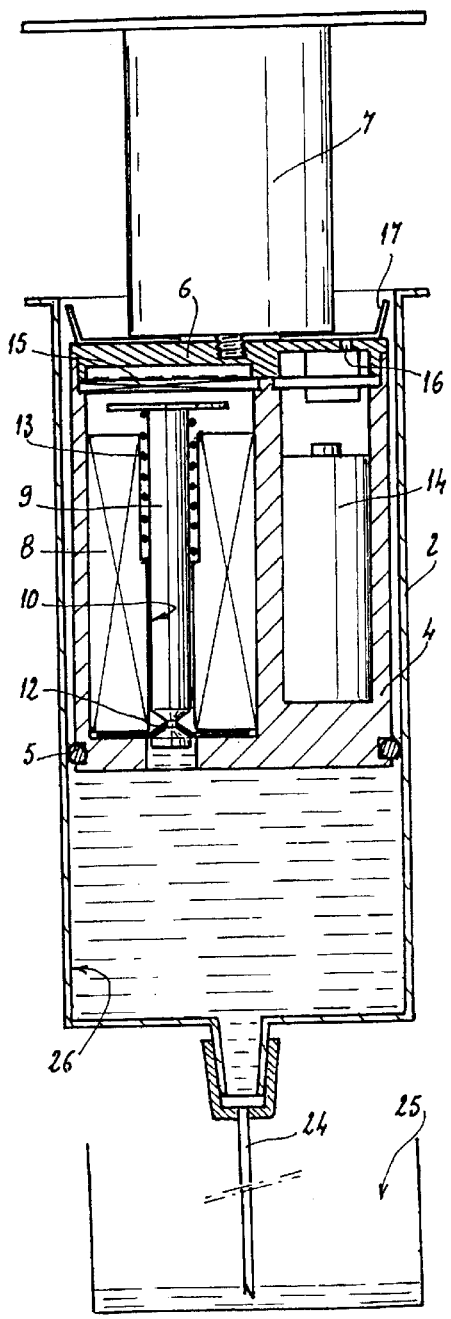

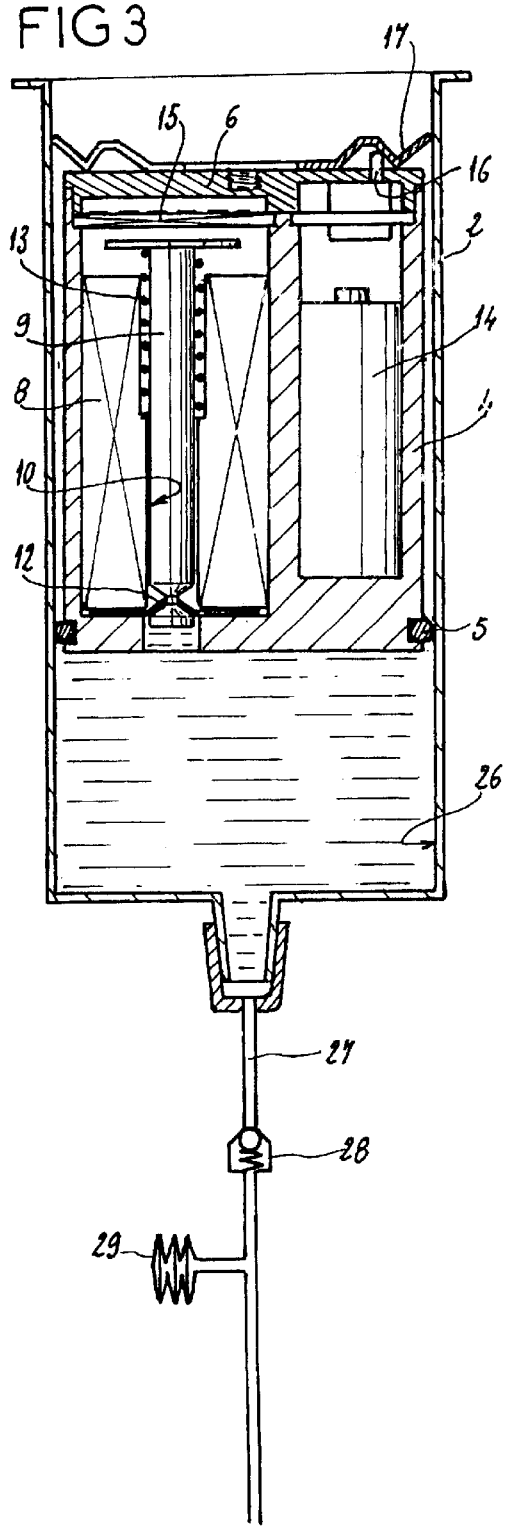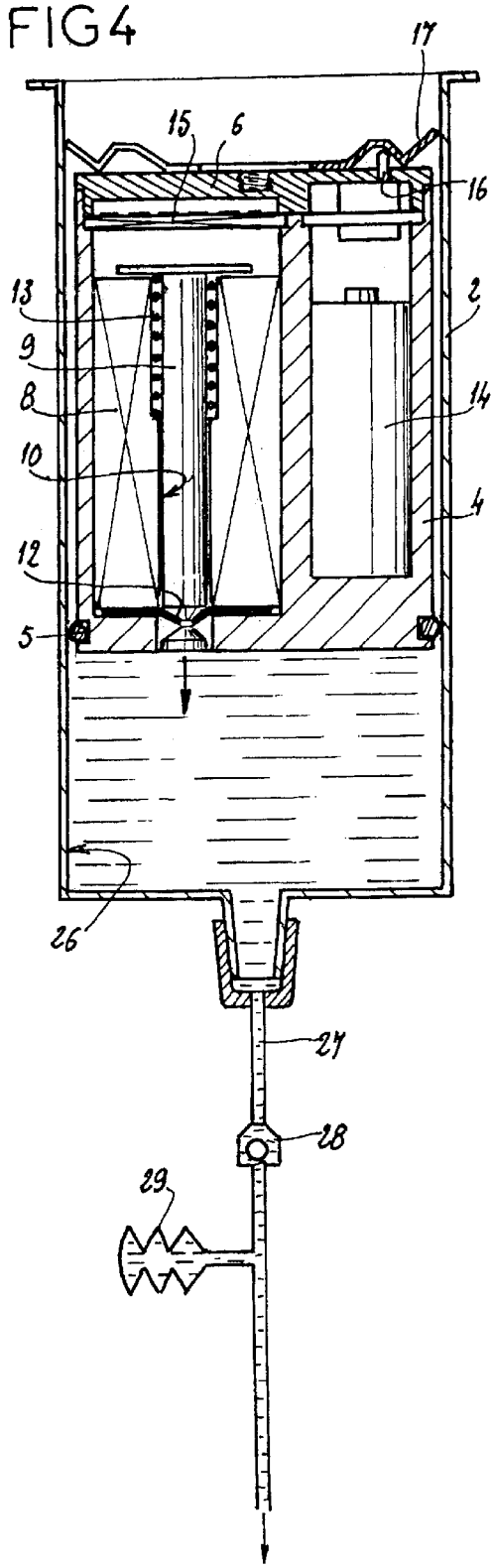

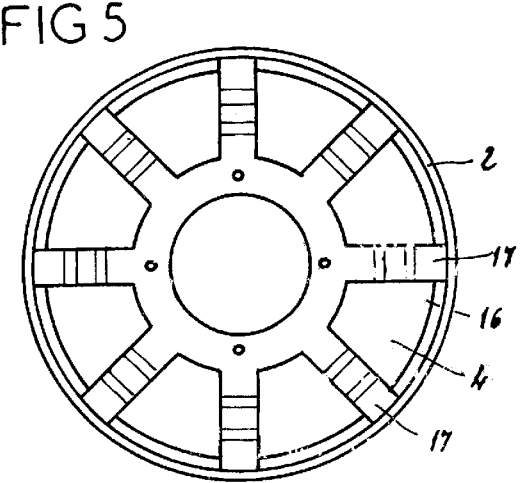
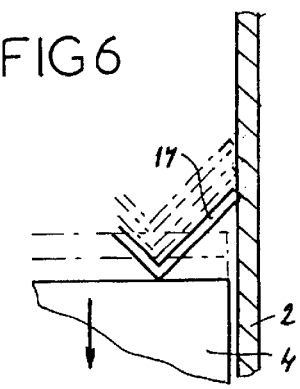
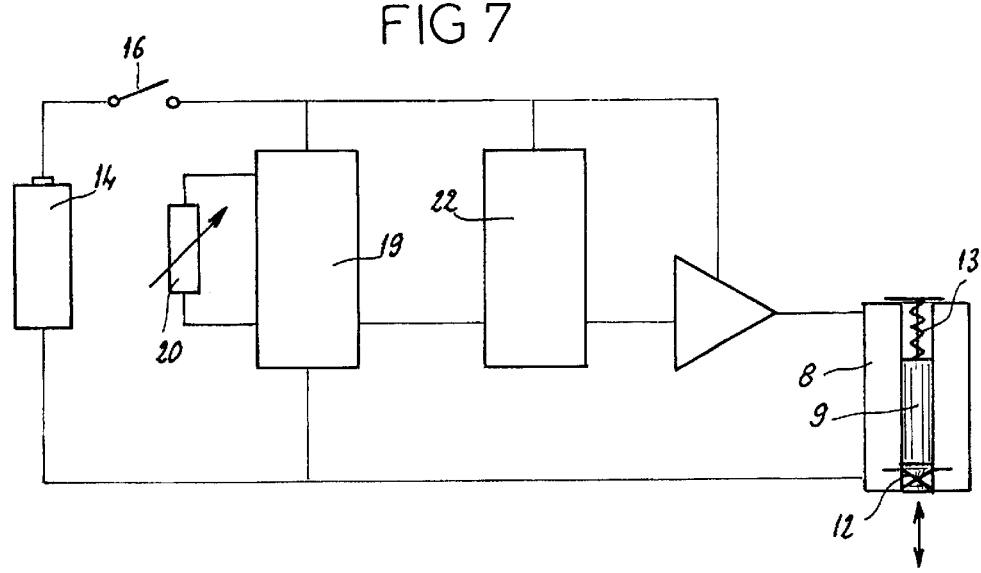

DEVICE FOR AMBULATORY INJECTION WITH CONTROLLED FLOW RATE OF A MEDICINE IN LIQUID FORM

TECHNICAL FIELD

The subject of the present invention is a device for injecting a medicament in liquid form at controlled flow rate into an ambulant. In the case of certain treatments, it is necessary to inject a liquid medicament at a very low flow rate for a very long period of time. To avoid having to immobilize the patient, it is known practice for the patient to be fitted with a device which injects at a controlled flow rate, which he carries around on his person and with which he can move around.

BACKGROUND OF THE INVENTION

One known device comprises an elastic cuff made of silicone or latex forming a reservoir, contained inside a rigid chamber. A device of this kind has an inlet to allow the medicament to be injected into the elastic cuff using a syringe. This inlet is fitted with a non-return valve preventing the medicament from flowing out once the syringe has been disconnected. The medicament outlet towards the patient is via a second orifice of calibrated cross section. This orifice is connected to a line with which the patient is infused. When the patient is connected, the medicament flows with a flow rate which depends on the pressure generated by the calibrated cuff, on the cross section of the outlet orifice and on the viscosity of the liquid. A device of this kind on the one hand requires the use of a syringe to fill it and, on the other hand, does not infuse at a constant flow rate, especially when emptying the last third of the elastic cuff.

The object of the invention is to provide a device which injects at controlled flow rate, which does not require an intermediate syringe for filling it, which provides a constant infusion flow rate and which also allows the value of this flow rate to be adjusted.

SUMMARY OF THE INVENTION

To this end, the device to which the invention relates comprises:
- a syringe body equipped with an access which may be connected in succession to a filling member, such as a needle, and to an infusion line fitted with a non-return valve to allow liquid to pass from the syringe into the line,
- a housing mounted so that it can slide in leaktight fashion inside the body so as to vary the volume of a chamber which it delimits with the body of the syringe,
- an element which, forming a piston, mounted on the housing and in contact with the chamber, is able, according to its position, to create a raised pressure or reduced pressure in the chamber,
- automatic control means for moving the piston-forming element back and forth.

Initially, to fill the chamber, liquid is drawn in like in a conventional syringe, the sliding housing acting as a piston.

At a later stage, the syringe body is connected to an infusion line and the piston-forming element is actuated, successively creating a raised pressure and a reduced pressure in the chamber containing the liquid medicament. When a raised pressure is exerted, a certain amount of liquid is discharged through the infusion line, whereas when a reduced pressure is exerted by the piston, the housing moves in the body of the syringe in a direction which reduces the volume of the chamber, thus automatically adapting to the volume of liquid contained therein.

According to one advantageous embodiment of the invention, the housing contains an electromagnet with which there is associated a moving core plunger mounted so that it can slide in a bore opening in the face of the housing delimiting the chamber, the moving core plunger being moved in one direction by the electromagnet and in the opposite direction by return means.

In this case a sealing diaphragm is mounted between the end of the moving core plunger and the chamber.

The means of returning the moving core plunger consist of a spring, and the means for controlling the electromagnet consist of an electric pulse generator. It is possible to vary the duration and the frequency of the pulses by controlling the pulse generator using an oscillator generating a signal whose frequency is preset using a potentiometer.

Advantageously, the means of moving the piston-forming element are housed in the housing.

According to another feature of the invention, the end of the syringe body lying at the opposite end to the access is open and serves as a passage for an operating member in the form of a plunger mounted on the rear wall of the housing.

The plunger is not fitted until the phase of filling the body of the syringe, and is then removed for the infusion operation.

Advantageously, it is the removal of the plunger which causes the infusion device to begin operation.

To this end, mounted on the rear wall of the housing is a switch, placed in the supply circuit of the means for controlling the electromagnet, this switch being actuated by the plunger so as to deactivate the means for controlling the electromagnet when the plunger is fixed on the housing, and vice versa.

In order to prevent the sliding housing from moving back inside the body when the piston exerts a raised pressure inside the chamber, the housing has means preventing it from moving backwards during injection periods.

According to one embodiment, the means preventing the housing from moving backwards during injection periods consist of radial tabs fixed on the rear wall of the housing, facing outwards and intended to brace against the interior face of the body.

As the piston body has to be able to move backwards so that the syringe body can be filled, when the plunger is mounted, the tabs preventing the backwards movement have a number of successive inverse undulations, the free end of each tab being inclined backwards, and the plunger, when mounted on the housing, presses against a central undulation of each tab so as to uncouple the tabs from the wall of the syringe body.

According to another feature of the invention, the infusion line is equipped with an accumulator situated downstream of the non-return valve. The role of this accumulator is to instantly absorb the volume expelled upon each pulse, then to return the stored liquid to the patient. Its usefulness is all the greater, when the infusion line is of small diameter, because of pressure drops. This accumulator may consist of a simple elastic chamber.

BRIEF DESCRIPTION OF THE DRAWING

In any event, the invention will be clearly understood with the aid of the description which follows, with reference to the appended diagrammatic drawings which, by way of non-limiting example, depict one embodiment of this device.

FIG. 1 is a view in longitudinal section of this device prior to use,

FIG. 2 is a view in longitudinal section at the end of filling with liquid,

FIGS. 3 and 4 are two views in longitudinal section during two successive phases in the infusion, FIG. 5 is a plan view of the device for preventing the backwards movement of the housing, FIG. 6 is a side view on an enlarged scale of this device which prevents the backwards movement, FIG. 7 is a view of a block diagram illustrating the elements of the electronic control board.

DESCRIPTION OF THE PREFERRED EMBODIMENT

As shown in FIG. 1, the device comprises a syringe body 2, one end of which has an access 3 which can be connected to a filling member or to an infusion line. For this purpose, this access is of the locking Luer type. The opposite end of the syringe body 2 to the access 3 is open. Mounted so that it can slide inside the body 2 is a housing 4, sealing being achieved by means of a peripheral seal 5. A plunger 7 may be removably attached, by screw-fastening, to the wall 6 of the housing, which is at the opposite end to the access 3.

Housed inside the housing is an electromagnet 8 wit a piston-forming element 9. The piston-forming element, in one embodiment, is a plunger. Hereinafter, the piston-forming element is described as a moving core plunger or a moving plunger 9. In FIG. 1, the moving core plunger 9 can move parallel to the axis of the syringe 2 inside a bore 10 of the housing 4. The front end of the moving core plunger is at the front wall side of the housing, sealing being achieved by means of a diaphragm 12. When the electromagnet 8 is powered, the moving core plunger 9 is moved towards the front of the syringe. The moving core plunger is returned backwards by a helical spring 13.

The sliding housing also contains a battery 14 providing the electromagnet with electrical power and an electronic control circuit 15.

The electromagnet is powered via the electronic control circuit 15 by a circuit which contains a switch 16 actuated by the removable plunger 7. When the plunger is mounted on the housing 4, the switch 16 is open, whereas the switch closes as soon as the plunger is removed, as shown in FIGS. 3 and 4.

The automatic control means comprising the electromagnet 8, powered by the battery 14, performs the moving of the moving core plunger 9 back and forth.

The electromagnet 8, powered by the battery 14,performing the moving of the piston forming-element back and forth.

From a practical point of view, the electromagnet 8 is powered from the battery 14 through the switch 16 and an oscillator 19 which generates a signal whose frequency is preset by a potentiometer 20. This signal drives a pulse generator 22 intended to limit the duration of the control pulse transmitted to the electromagnet 8.

Prior to use, the device is in the position depicted in FIG. 1, the plunger 7 being mounted on the housing 4, and the access 3 being closed by a protective cap 23. Once the cap has been removed, a needle 24 is then mounted on the access 3. Liquid can therefore be drawn up from a container 25. The liquid then passes from the container into a chamber 26 located between the sliding housing 4 and the body 2 of the syringe. The needle 24 is removed and replaced with an infusion line 27. The operator removes the bubbles of air from the chamber 26 and from the line 27. The line 27 has a non-return valve 28 which allows liquid to pass only from the device to the patient, and has an accumulator 29 located downstream of the valve 28.

Once the line has been connected to the patient, the plunger 7 is removed by unscrewing. This operation closes the switch 16 and thus supplies power to the electronic circuit and to the electromagnet 8. Infusion begins.

The pressure needed for intravenous infusion is a minimum of 30 mbar (1 bar=101 300 Pa). The device depicted is designed to be able to supply a pressure of 100 mbar.

When the electromagnet 8 is energized with electrical current, the core plunger 9 is attracted to a forward position until it reaches the end of its travel. The stroke of the core plunger and its diameter determine the volume of liquid displaced for each pulse. When the core plunger 9 moves forward, it exerts a raised pressure in the chamber 26, such that the volume available therein decreases. As the liquid is incompressible, it is delivered to the infusion line 27, provided the raised pressure generated is lower than the pressure needed to cause the housing to move backwards. To avoid such risks, the tabs 17 for preventing backwards movement fulfill this function of preventing such backwards movement, as explained previously and as depicted in FIGS. 3 to 6.

At the end of the pulse, the moving core plunger 9 moves back under the action of the return spring 13. A reduced pressure is created in the chamber 26. As the liquid in the line cannot be drawn back in because of the non-return valve 28, it is the housing 4 assembly which advances towards the front end of the syringe body.

As is clear from the foregoing, the invention provides a vast improvement to the state of the art by providing a device for injecting at a controlled flow rate into an ambulant which is of a simple structure, which can be filled with liquid autonomously and which provides a constant and adjustable flow rate throughout its emptying.

As goes without saying, the invention is not restricted to the single embodiment of this device which has been described hereinabove by way of example; on the contrary, it encompasses all variations. Thus, in particular, the element which successively raises the pressure and reduces the pressure in the chamber containing the liquid could consist not of a piston mounted to slide in a bore, but of a diaphragm deformed successively in two opposite directions, without in any way departing from the scope of the invention.

What is claimed is:

1. Device for injecting a medicament in liquid form at a controlled flow rate into an ambulant, comprising:
    a syringe body having an access at one end thereof to allow liquid to pass from the syringe;
    a housing mounted slidably in leaktight fashion inside the body so as to vary a volume of a chamber which the housing delimits with the body of the syringe;
    a piston-forming element, mounted on the housing and in contact with the chamber, wherein the piston-forming element is moveable relative to the housing, the piston-forming element creating a raised pressure or reduced pressure in the chamber according to a position of the piston-forming element; and
    automatic control means for moving the piston-forming element back and forth.
2. The device according to claim 1 wherein the means of moving the piston-forming element are housed in the housing.

3. The device according to claim 1 wherein the end of the syringe body lying at the opposite end to the access is open and serves as a passage for an operating member in the form of a plunger mounted on the rear wall of a housing.

4. The device according to claim 3 wherein mounted on the rear wall of the housing is a switch, placed in a supply circuit of means for controlling the electromagnet, the switch being actuated by the plunger so as to deactivate the means for controlling the electromagnet when the plunger is fixed on the housing, and vice versa.

5. The device according to claim 1,
wherein the housing has means preventing backwards movement of the housing during injection periods.

6. The device according to claim 5, wherein the means preventing the housing from moving backwards during injection periods consist of radial tabs fixed on a rear wall of the housing, facing outwards and intended to brace against the interior face of the body.

7. The device according to claim 6, the tabs preventing the backwards movement have a number of successive inverse undulations, the free end of each tab being inclined backwards, and a plunger, when mounted on the housing, presses against a central undulation of each tab so as to uncouple the tabs from the wall of the syringe body.

8. The device according to claim 7,
wherein the housing has means preventing backwards movement of the housing during injection periods.

9. The device according to claim 8,
wherein the means preventing backwards movement of the housing during injection periods consist of radial tabs fixed on a rear wall of the housing, facing outwards and intended to brace against an interior face of the body.

10. The device according to claim 9,
wherein the radial tabs have a number of successive inverse undulations, a free end of each tab being inclined backwards, and a plunger, when mounted on the housing, presses against a central undulation of each tab so as to uncouple the tabs from the wall of the syringe body.

11. The device according to claim 1,
wherein the access is connected to an infusion line, and liquid passes from the syringe body into the infusion line.

12. The device according to claim 11,
wherein the infusion line is equipped with a non-return valve fitted thereon, and an accumulator positioned downstream of the non-return valve.

13. Device for injecting a medicament in liquid form at a controlled flow rate into an ambulant, comprising:
a syringe body having an access at one end thereof to which an infusion line is connected so as to allow liquid to pass from the syringe into the infusion line;
a housing mounted slidably in leaktight fashion inside the body so as to vary the volume of a chamber which the housing delimits with the body of the syringe; and
a piston-forming element, mounted on the housing and in contact with the chamber, creating a raised pressure or reduced pressure in the chamber according to a position of the piston-forming element,
wherein the housing contains an electromagnet with which there is associated the piston-forming element slidably mounted in a bore opening in a face of the housing delimiting the chamber, the piston-forming element being moved in one direction by the electromagnet and in the opposite direction by return means.

14. The device according to claim 13 wherein a sealing diaphragm is mounted between the end of the piston-forming element and the chamber.

15. The device according to claim 13 wherein the means of returning the piston-forming element consist of a spring.

16. The device according to claim 13 wherein the means for controlling the electromagnet consist of an electric pulse generator.

* * * * *

UNITED STATES PATENT AND TRADEMARK OFFICE
CERTIFICATE OF CORRECTION

| | | |
|---|---|---|
| PATENT NO. | : 6,416,498 B1 | Page 1 of 1 |
| APPLICATION NO. | : 09/462288 | |
| DATED | : July 9, 2002 | |
| INVENTOR(S) | : Pierre Frezza | |

It is certified that error appears in the above-identified patent and that said Letters Patent is hereby corrected as shown below:

Column 3,
Line 26, after "8" delete "wit" and insert therefor -- with --,
Line 50-53, delete "The electromagnet 8, powered by the battery 14, performing the moving of the piston forming-element back and forth.",
Line 53, insert -- The rear wall 6 of the housing is equipped, as shown in particular in Figures 5 and 6, with a number of non-return tabs 17 which are metal tabs with several undulations. The free end of each tab faces outwards and backwards and is intended to press against the interior wall of the body of the syringe. The tabs 17 can be retracted by pressure on the removable plunger 7, when this plunger is mounted on the housing, as shown in Figures 1 and 2. --

Column 4,
Line 65, after "the" (second occurrence) insert -- automatic control --.

Column 5,
Line 19, after "6" insert -- wherein --.

Signed and Sealed this

Thirty-first Day of July, 2007

JON W. DUDAS
*Director of the United States Patent and Trademark Office*